United States Patent [19]

Villa-Real

[11] 4,293,845

[45] Oct. 6, 1981

[54] ELECTRONIC MULTI-PATIENT MEDICATION-TIME-INTAKE PROGRAMMER AND ALARM SYSTEM

[76] Inventor: Antony-Euclid C. Villa-Real, 2512 Capistrano Ave., Las Vegas, Nev. 89121

[21] Appl. No.: 141,127

[22] Filed: Apr. 17, 1980

[51] Int. Cl.³ .................................................. G08B 7/00
[52] U.S. Cl. .............................. 340/309.3; 340/309.1; 340/309.4
[58] Field of Search .......................... 340/309.3, 309.4; 368/10; 221/2

[56] References Cited

U.S. PATENT DOCUMENTS 4,223,801  9/1980  Carlson .................................. 368/10

*Primary Examiner*—Harold I. Pitts

[57] ABSTRACT

A pocket-size Electronic Multi-Patient Medication-Time-Intake Programmer and Alarm System for use in homes, offices, clinics and hospitals in order to properly program a plurality of patients taking a singular or a plurality of medications, respectively, based on the desired time interval or frequency in hours as well as the duration in days; the device has a memory system in which all the program data during the certain time frame becomes stored and utilized to trigger the alarm system of the device to give the patient or the individual taking care of the patient or patients, the correct indication of the patient identification and the medicine identity to be taken at the particular instant when the alarm sounds, by sliding a switch to a "READ" position thus displaying all the relevant data into the proper LED or LCD displays; the device has the capability of shutting off the alarm system when alarm sounds are not desired to commence, especially during night-time rest of the patient without affecting the internal progression of the succeeding scheduled time and day of medication-intake of the singular or multiplicity of patients as well as singular or a plurality of medications. The device is capable of registering the actual time and actual date by pushing the corresponding function key; the time and date can be programmed by the user to respond to the actual time and date at any time desired.

22 Claims, 4 Drawing Figures

ELECTRONIC MULTI-PATIENT MEDICATION-TIME-INTAKE PROGRAMMER AND ALARM SYSTEM

BACKGROUND OF THE INVENTION

This invention relates to a pocket-size, hand-held, Electronic Multi-Patient Medication-Time-Intake Programmer and Alarm System to aid and correlate in the taking of medicine by one or more individuals.

In order to maintain the proper pharmacological effectivity of medicines to the individual patient or group of patients, the drugs, whether they may be of a prescription or non-prescription nature, must be administered on the correct scheduled time-intake per specific drug-dosage per patient, so that the therapeutic levels of each of the medication can be maintained at an optimal strength in the body or at specific parts of the body. Some medicines may be taken in a matter of hour intervals, such as every 3 or 4 or 6 or 8 or 12 hours per day; others may be taken once a day or every other day for a certain number of days duration or continued indefinitely. Since modern drugs take the form of factory pre-set therapeutic strengths packed in the form of tablet, capsule, liquid (administered in teaspoonfuls) or suspended in injectible liquids (administered in cc.), and there are occasions wherein the called for drug potency per drug intake may be ½, 1, 2, 3, or more of any of the drug forms, the systematic application of the Electronic Multi-Patient Medication-Time-Intake Programmer and Alarm System can well serve the purpose of efficiently solving the problems of committing errors in the administration of both singular and multiplicity of medicines for either one or a plurality of patients in the homes, offices, hospitals, and during travel. The commonly encountered errors in giving the incorrect dosages, incorrect medicines, medicines given to the wrong person at the wrong time, and medicines given after it should have been discontinued, can all be prevented by the use of the instant invention.

SUMMARY OF THE INVENTION

The medication reminder of this invention has been designed to assist an individual or group of individuals in taking a single or plurality of medications based on a desired time interval and dosage and to alert the individual or group of individuals as to the medication identity and to the correct time for taking the medication as it becomes due.

Thus, it is one object of the present invention to provide a pocket size, hand-held, electronic alarm system for use in conjunction with the dispensing of medication to one or more persons.

Another object of the present invention is to remind the person or persons to take their medication by the generation of an audible signal.

Another object of the present invention is to provide a device in which either a single or number of different medicaments may be programmed to be taken with the time intervals not necessarily being equal, but of such magnitude as desired or prescribed.

A further object of the present invention is to provide a medication reminder device having an indicating means to enable the person or persons to readily determine how many times the particular dosage of each kind of medicine has been taken during the course of drug therapy.

A still further object of the present invention is to provide visual displays indicating the type, frequency and duration of the medicine taken or to be taken by a specific patient.

A still further object of the present invention is to provide a medication reminder device in which at the programmed time, an audible alarm signal is generated and continues until the person terminates the alarm thereby indicating that medication is due.

Yet a further object of the present invention is to provide an electronic system to aid in the taking of medication and in which data for one or more than one medication may be quickly ascertained.

Yet a further object of the present invention is to provide an electronic system to monitor medication intake and to allow for the simple and easy programming of the alarm cycle.

The above and other objects, advantages and features of the present invention will become more apparent from the following detailed description taken in conjunction with the accompanying drawings.

DETAILED DESCRIPTION OF THE DRAWINGS

Figure 1:
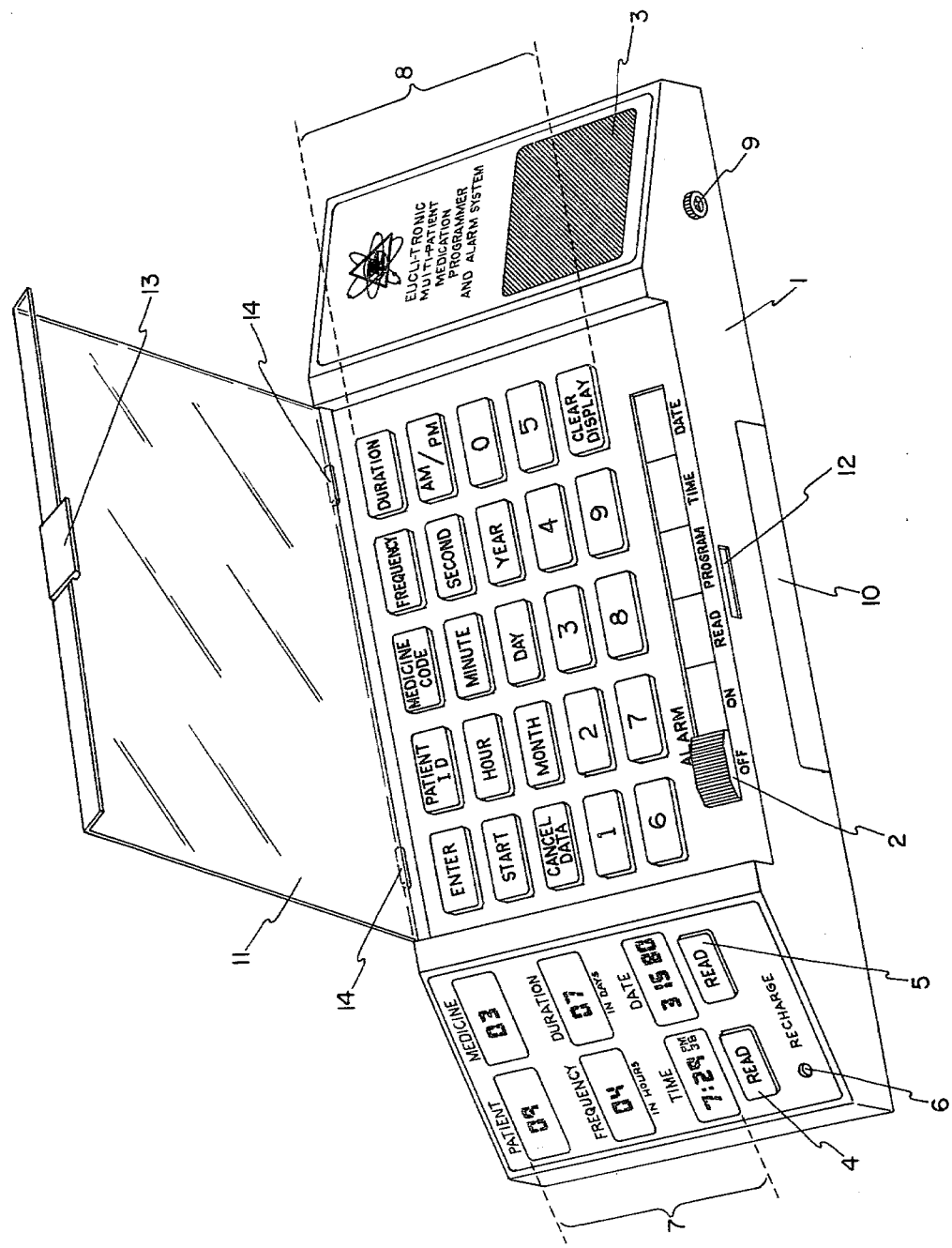
FIG. 1 is a perspective elevational view of the device according to one embodiment of this invention.

Referring to FIG. 1, there is shown a preferred embodiment of the instant invention generally at 1 in the form of a hand-held rectangular housing. A selector slide switch 2 is shown in the "OFF" position. The speaker 3 provides means for emitting the audible signal when in use. At 4 and 5 are shown the "READ" keys for the respective visual LED or LCD display readout information for time and date, respectively, included in the digital displays in group 7.

The corresponding "READ" keys 4 and 5 for "TIME" and "DATE" being particularly used only when one desires to use the device as a timepiece or a calendar, respectively. All information in group 7 such as the displays for "PATIENT NUMBER", "MEDICINE CODE", "FREQUENCY (in hours)", "DURATION (in days)", "TIME" and "DATE" are made to appear at these respective displays once the slide switch has been switched from the "ALARM" position, to the "READ" position, or has been switched to the "PROGRAM" position during the writing of the appropriate programmable data to the RAM memory of the device.

The various input function keys shown at 8 and their use in operation will be hereinafter discussed. The device is capable of being powered by 110 volt current and a jact socket 9 is provided for such use. The preferred use is by battery power and at 10 is provided storage space for such batteries. A recharge indicator 6 is provided and will signal when battery power is at an insufficient level to support operation of the device.

In operating the electronic Multi-Patent-Medication-Time-Intake Programmer and Alarm System of FIG. 1, it is necessary to set the clock by sliding the main selector switch 2 to the "TIME" position and then by touching and/or depressing the corresponding numerical keys 8, enter the time into the device. The time will then be displayed in the LED or LCD "TIME" display window included in group 7.

To set the date, slide the main switch to "DATE" position, push "MONTH" key and enter the number of the present month (two digits). Push "DAY" key and enter the number of the present day (two digits). Push "YEAR" key and enter the number of the present year (two digits). All this information is displayed on "DATE DISPLAY" shown at group 7. Then push the "ENTER" key. The calculator stores this information in the memory unit (RAM). The device is now programmed for running at 31 days per month. Months having less than 31 days are required to be reset unless pre-programming has already been set for a certain duration such as in the next five years or so at the (ROM) memory unit starting from the activated actual date.

To enter the program desired, move the slide switch to "PROGRAM" position, push the "I.D." key and enter the patient's I.D. number. Push the "MED" key and enter the code number of the medicine to be taken, push the "FREQUENCY" key, and enter the numerical key which will indicate the hourintervals required for taking the medication. Push the "DURATION" key and enter how many days required to complete the intake of the particular medication. Then push the "START" key and enter at what time the first dose of the particular medicine should be taken. Upon pushing "ENTER" key, the device stores all information required for doing the work, so that the calculator is now programmed and ready for the successive medication-time-intake interval for the particular patient as well as the particular coded medicine. Then move the slide switch to "ALARM ON" position. Now, the display is off, but the device is working internally because there is an independent switch that is internally located near the battery pack which is in the "ON" position. When the device is not in use, this internal switch is turned "OFF".

To operate the "READ" function of the device, when the slide switch is in normal "ALARM ON" position, and the alarm sounds through the speaker, the switch must be moved to "READ" position. Immediately all information required is shown at the proper LED or LCD displays. By sliding the switch from "ALARM ON" to any other position, the sound from the speaker is stopped. The information on the displays show the patient's I.D. number, the code number of the medicine, the frequency (in hours) of the medicine, and the duration (in days) or number of days needed to take the medicine. After the particular person takes the specific medication called for at the time, the user then must move the slide switch back to "ALARM ON" position to proceed to the next medication to be taken as scheduled depending upon the programmed data. In this position, the display is off but the device is running internally, and again ready for the next alarm to commence.

In this simple embodiment which requires the patient's I.D. number as well as the medicine code number, it is ideal that each patient be given special numbered tags and each particular medicine be given respective identification numbers by writing the specific number of the medicine container with an indelible marker or by attaching a special color coded self-adhering, numbered paper or tape, at the side of the particular medicine container.

Figure 2:
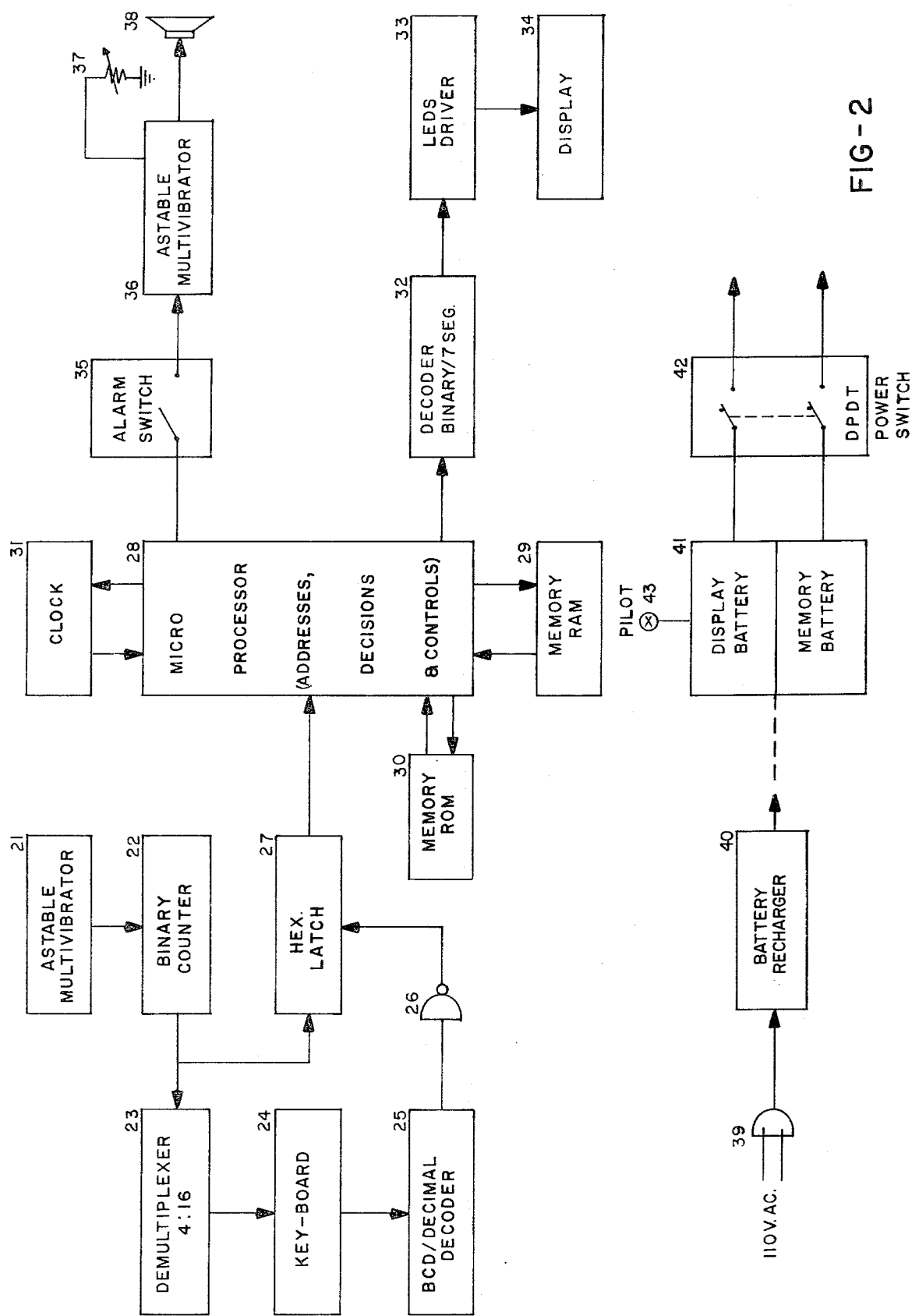
FIG. 2 is a block diagram of the electronic system for the device shown in FIG. 1.

Referring to FIG. 2, there is shown in block diagram the electronics system for the device shown in FIG. 1. When the slide switch 2 is moved to "PROGRAM" position, immediately the astable multivibrator 21 begins to send a train of pulse signals with a prefixed frequency to the binary counter 22; this circuit counts the pulses and transforms them into a binary form (4 bits), and sends them to the demultiplexer 23; it activates one of sixteen possible outputs and depending upon which key is depressed on the key-board 24, it activates the code number of that key and sends it to the decoder 25 which transforms it to decimal code and sends it through NAND gate 26 to hex latch 27. The combination of these two inputs on hex latch 27 gives the value and address of the key depressed. All the information is latched into this circuit until the "ENTER" key is pushed, so the information is sent to microprocessor 28 and this sends the information to the memory (RAM) 29 or to the clock 31 or to the display 34 depending which function is being used. The microprocessor 28 decides where to send the information from the keyboard: If the data is about the patient's code number or code number of medicine or frequency of the medicine or duration (in days) for taking the medicine, these are sent to the memory RAM (random access memory) 29 to be used by the microprocessor 28 at a later time when the alarm sounds; if the data coded is about the setting of the clock 31, the microprocessor 28 sends the time and date to the clock. The memory ROM (read only memory) 30 is pre-programmed in the factory providing the step by step sequence of instructions that the microprocessor 28 will use in deciding what and when to do with each specific instruction.

Every moment, the microprocessor 28 is proceeding in comparing the information present on the clock with the information stored in the memory RAM 29, so that when both of them coincide and the alarm switch 35 is on, the microprocessor sends a signal to the astable multivibrator 36 for turning on the audible signal. This circuit drives the speaker 38 which sounds with a pre-adjusted tone or frequency, but this frequency may be changed by setting the variable resistor 37.

When the alarm switch 35 is at the "ON" position and the alarm 38 sounds, the user must move the slide switch to the "READ" position for stopping the sound and for reading the information. All data is sent to 32 which converts the binary data into seven data segments, and then is sent to the LEDS driver 33 which amplifies the signal to be used and is able to lead the display 34 which shows all data at desired time.

This instrument is to be powered by a permanent battery because its memory, microprocessor and clock are working continuously. The supply 41 contains two different sets of batteries. One for continued supply of energy (memory battery) and the other for the electrical energy supply to the input and output circuits (display battery). At 42 is a double pole double terminal switch that acts as a power switch and it needs to be at the "ON" position at all times when the instrument is in use.

The option of turning off the alarm at any period of time is provided, by moving the slide switch to "ALARM OFF" position but in this position the device still continues to work internally.

Any or all information can be erased before it is entered into the memory or before depressing the "ENTER" key, ordering the device to erase by depressing the "CLEAR" key.

In order to cancel the data or a certain medication being taken by a particular patient, it is necessary to wait until the alarm rings and then slide the switch to "READ" position, and when the data appears, press the function key marked "CANCEL DATA" and all data relevant to that particular medicine taken by that specific patient will be cancelled from the microcomputer's memory, so that the system will not be activated to alarm again. This procedure is followed when one wishes to discontinue a particular medication of the specific patient.

Figure 3:
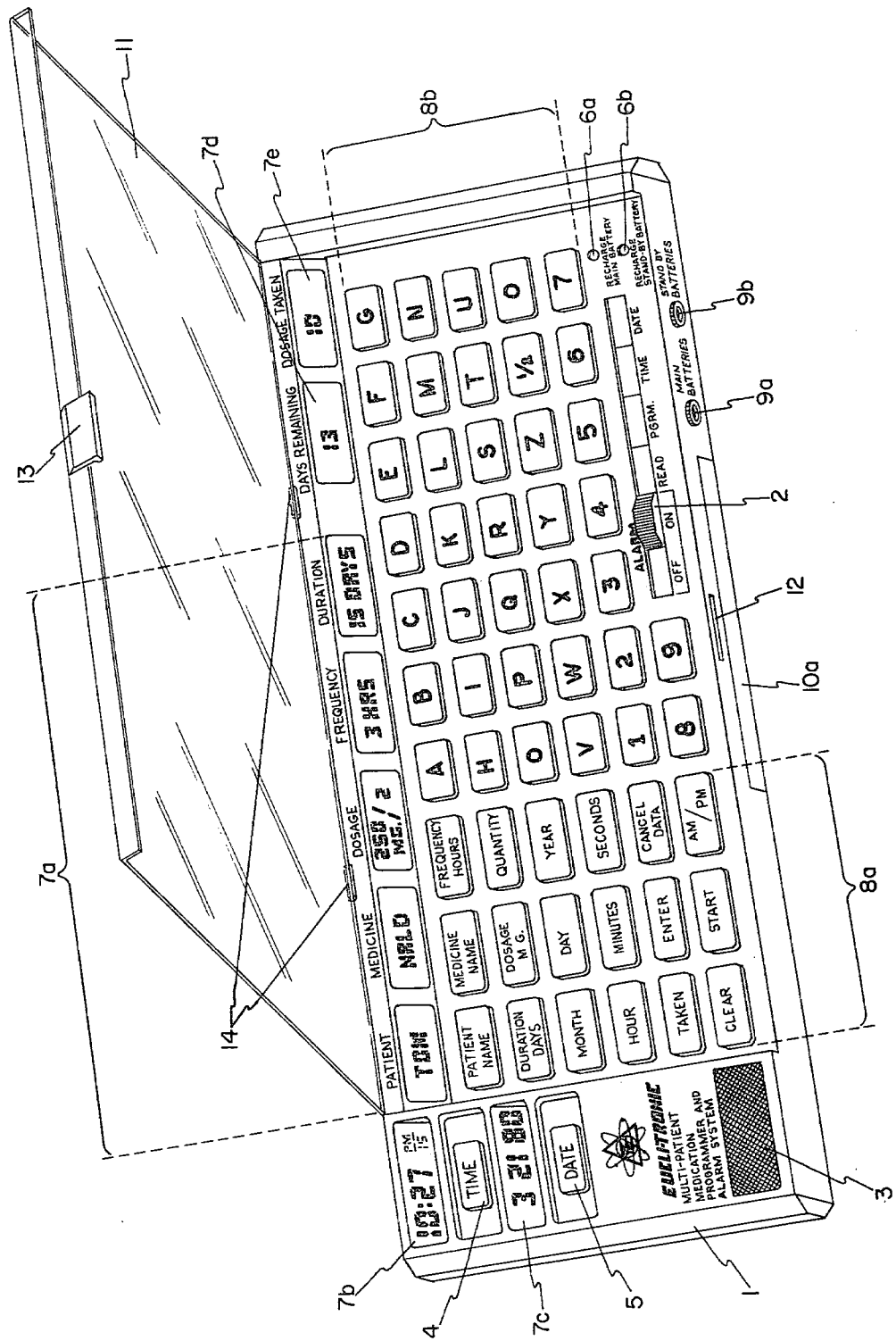
FIG. 3 is a perspective elevational view of an alternative embodiment of the present invention.

Referring to FIG. 3, there is shown a second embodiment of the present invention generally shown at 1a in the form of a hand-held rectangular housing. A selector slide switch 2a is shown in the "ON" position. The speaker 3a provides means for emitting an audible signal when in use. At 4a and 5a are shown the time and date keys, respectively, which activates the LED or LCD time and date display 7b and 7c, respectively. The various input function keys are shown at 8a and operate in a manner generally similar to the input function keys of the device of FIG. 2. At 8b is shown alphabet keys from A to Z and numerical keys from integers 0 to 9, and a fraction number of ½.

This device also provides visual display information relating to "DAYS REMAINING" at 7d which numerically indicates the number of days left for the user to take the prescribed medication. Also at 7e is provided visual display information indicating "DOSAGE TAKEN" which would numerically indicate the number of dosages already taken by the user of a particular kind of medication. At 7f is indicated the dosage amount of the prescribed medication, for example, the dosage in milligrams of medicine per tablet per capsule or per teaspoonful, followed by the information of the quantity or number of tablets or capsules or teaspoonfuls per intake, depending upon the drug form.

In addition to the main battery recharge indicator 6a, which will light when the sets of main batteries are at an insufficient level, there is also provided, a stand-by battery recharge indicator 6b, also capable of emitting a light signal when the stand-by sets of batteries are running low, to support the operation of the device. When the main battery power has reached a level insufficient to power the device, the stand-by battery is automatically switched into service by means of an electronic flip-flop circuit. The battery power of this device can be augmented as in FIG. 1 by 110 volt current which can be introduced by means of jack sockets 9a and 9b when battery power for either is insufficient. In order to recharge the connected sets of batteries and at the same time enable the operation of the device by the use of the commercial home power.

The main difference between this embodiment and the first embodiment is that the first embodiment uses code numbers for the patient and code numbers for the medicine, while this embodiment uses letters for the patient and letters for the medicine. Also, this embodiment provides additional information relating to "DAYS REMAINING" "DOSAGE" and the number of "DOSAGE TAKEN."

After performing the program for both the time and date, in the manner already described in the first embodiment, the user now programs for the "Patient" and "Medicine" in the following manner:

(1) Slide the function switch to "PROGRAM" position, then push the "PATIENT NAME" keys and enter the first 3 or 4 letters of the patient's name.

(2) Next, push "MEDICINE NAME" key and enter the first 4 letters of the medicine. (3) Then, push "FREQUENCY" key and enter how often (in hour intervals) the patient is to take the medicine.

(4) Thereafter, push "DURATION" key and enter how many days the patient is to take the medicine.

(5) Push "DOSAGE" key and enter the dosage prescribed by the physician (example 250 mg.).

(6) Then, push "QUANTITY" key and enter the required number using the relevant numerical keys such as ½, 1, 2, or 3, etc. of the dosage form (already expressed in milligrams) in case of tablet, capsule or liquid (in teaspoonful) to indicate for example, such actual dosage per intake of ½ tablet of 250 mg.-tablet dosage form or 2 tablets of the 250 mg.-tablet form, etc. whatever the medication form may be which is known by the user, by checking on the particular medicine form in each medicine container.

(7) Push "START" key and enter at what time the device must begin to count, using the coordinated function keys for "HOUR" and "MINUTE" followed by the corresponding numerals called for to indicate the hour and minutes for starting the medication intake.

(8) Finally, push the "ENTER" key to enter all information into the microcomputer's memory.

Figure 4:
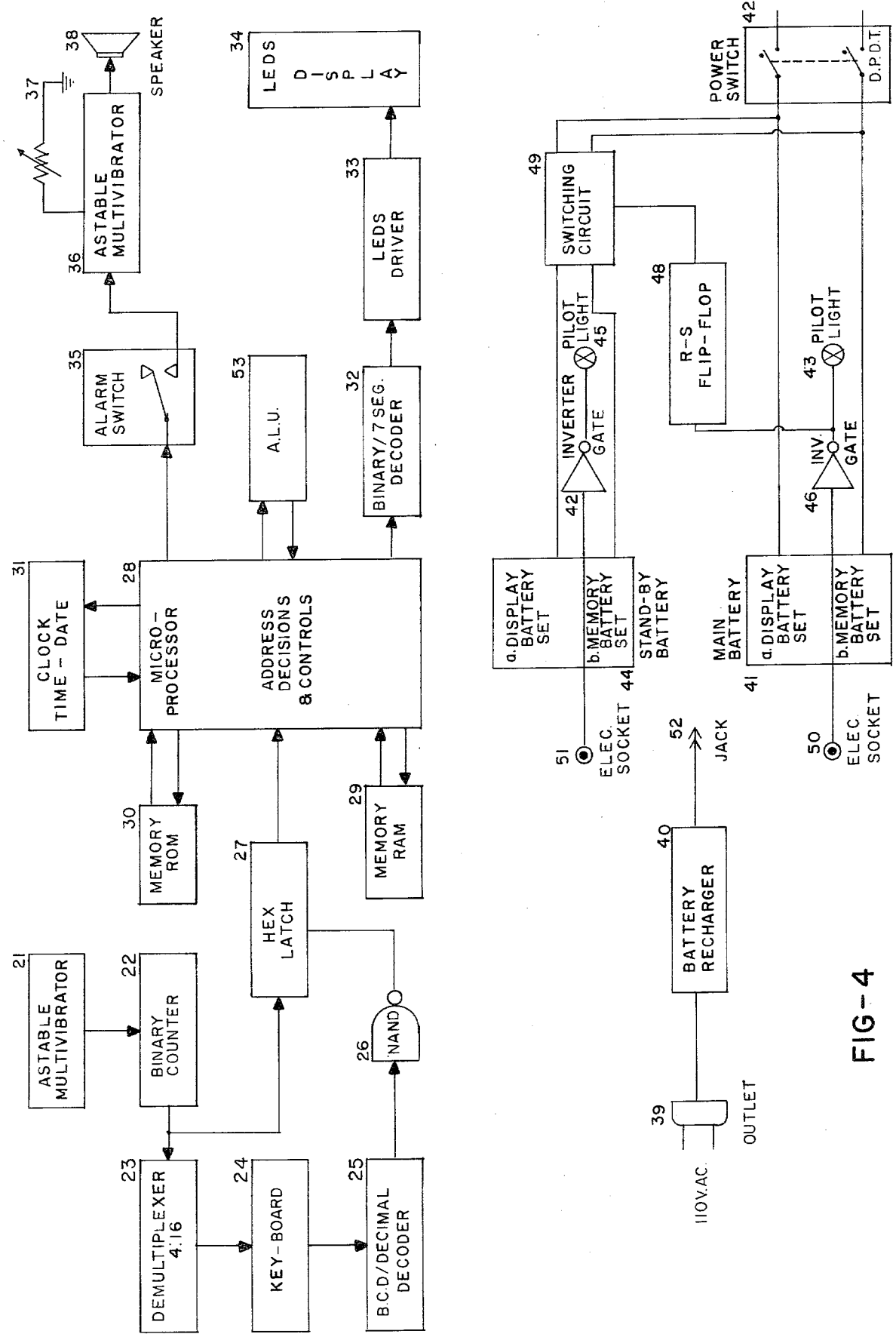
FIG. 4 is a block diagram of the electronic system for the device shown in FIG. 3.

The main difference in the block diagram of FIG. 4 is the additional circuit 53 or "ARITHMETIC LOGIC UNIT" (A.L.U.), and its function. This unit assists the microprocessor to obtain the information about the remaining number of days left for one to take a certain medicine, and also to provide the number of dosages already taken by the patient pertaining to a particular kind of medicine.

This A.L.U. circuit 53, subtracts one from the duration (expressed in number of days), every 24 hours from the starting time of actual programmed medication-time intake of each particular kind of medicine entered into the microcomputer, to give the data for the remaining days. The A.L.U. circuit 53 also adds one to the number of dosages already taken every time the patient takes a particular medicine, by depressing the "TAKEN" key in order to give the updated number of dosages already taken.

This information is relayed to the microprocessor which addresses and changes the stored previous information by the just entered new information, and retrieves the updated relevant information ready for display when called for on the indicated time and day during the administration of that particular medication for that specific patient.

The main batteries 41 consist of (a) display battery set which is for the purpose of giving energy to both the function keys as well as to the display registers, having LED or LCD visual displaying means and; (b) a memory battery set which supplies the energy for powering the continuous operation of the internal clock and calendar as well as for supplying electrical power to the microprocessor and both the RAM and ROM components. When these main batteries 41 reach a level of insufficient electrical power to operate the device, the "INV. GATE" 46 is activated to trigger the activation of the pilot light 43 and at the same time, the R-S FLIP-FLOP circuit 48 which is a Bi-stable circuit becomes activated to automatically trigger the SWITCHING CIRCUIT 49 so that additional electrical energy is automatically drawn from the STAND-BY BATTERY sets 44 to provide the adequate power supply to operate the device. During the time in which the STAND-BY BATTERIES are supplying the electrical power to the system, the main batteries 41 are recharged by attaching the electrical jack 52 to electrical socket 50, while the device is connected to a 110 V.AC. power through electrical plug 39, passing through the battery recharger 40. The main batteries can also be replaced with new sets of batteries in case the user desires not to use a battery recharger. During this replacement there will be no loss of operational capabilities while the device is in use, because of the substituted electrical power, automatically coming from the stand-by set of batteries 44, due to the automatic activation of the R-S FLIP-FLOP circuit 48. The device is also provided by another INVERTER GATE 47 to trigger the LED pilot light 45 of the stand-by batteries when the said stand-by batteries are running low in electrical power, so that the stand-by batteries can also be re-charged by the battery recharger 40 by connecting the electrical jack 52 to electrical socket 51 when the electrical plug 39 of the battery recharger is connected to the home commercial power source. Like the main batteries, the stand-by batteries can also be replaced by new sets. The power switch 42 which is a double-pole, double-terminal power switch is situated internally near the battery pack so as to effect an "ON" position when the device is in use, and can be turned off when the device is not being used. The reason for this power switch 42 to be located internally is to safeguard against the accidental turning off of the device from the main keyboard at the face of the calculator when the said power switch 42 is in the "ON" position during the operation of the device.

Another embodiment which is not shown in the drawings is the possible addition of function keys such as; (1) for tablet; (2) for capsule; (3) for liquid (in teaspoonfuls) and; (4) for injection in cc. in order to properly delineate each kind of medication being used, especially where there are many patients involved as in hospitals. The corresponding displays for these additional function keys can also be provided.

In order to protect the desired operation of the device in the two embodiments in FIGS. 1 and 3 respectively the function keys including the slideable switch 2 are covered by a transparent cover 11, being of a hinge type having hinge structure 14; said cover placed in covering position by the use of a mechanical latching means 13 accommodated through groove 12 of the main body frame.

From the descriptions of the embodiments and the electronics block diagram of the present invention, there can be other obvious modifications and variations in the light of the aforementioned teachings, therefore it is to be understood that within the scope of the appended claims, the instant invention may be practiced otherwise than as specifically described.

I claim:

1. An electronic monitoring and alarm system for the time-intake of medications, comprising program entry and storage means for entering and storing a selected frequency of time, and for entering and storing a selected type of medication means for converting said selected frequency and medication to a visual display thereby permitting instant recognition of the programmed data, sequencing means for receiving a start signal and being responsive to clock signals, means responsive to the sequencing means and selected frequency data for producing an audible signal, thereby indicating that the programmed frequency of time for the selected medication has elapsed.

2. An electronic monitoring and alarm system according to claim 1, wherein the program entry means includes a stable multivibrator with a prefixed pulse signal connected to a binary counter.

3. An electronic monitoring and alarm system according to claim 1, wherein the stored information is recalled and visually displayed by the manual activation of a switch.

4. An electronic monitoring and alarm system according to claim 1, wherein a plurality of selected time frequencies and medications can be stored in the device for recall at a later time.

5. An electronic monitoring and alarm system according to claim 1, wherein all program entry data is converted into binary data and then converted into LED or LCD visual display.

6. An electronic monitoring and alarm system according to claim 1, wherein a single person or group of persons can be monitored by the programmed entry of individual identification codes.

7. An electronic monitoring and alarm system according to claim 6, wherein a single or plurality of medications can be monitored by the programmed entry of medication codes.

8. An electronic monitoring and alarm system according to claim 1, wherein the audible signal means is generated through a speaker with a preadjusted tone.

9. An electronic monitoring and alarm system according to claim 1, wherein the device is battery powered and includes a stand-by or back-up battery system activated for automatic supply of electrical energy when the main battery is running low in electrical power.

10. An electronic monitoring and alarm system according to claim 5, wherein the visual display of the data is in numerical form.

11. An electronic monitoring and alarm system according to claim 5, wherein the visual display of the data is in alpha-numeric form.

12. An electronic multi-medication time-intake and alarm system comprising a hand-held, generally rectangular housing having thereon a plurality of program entry means for entering and storing a selected frequency of time, a selected type of medication and a user identification code, means for converting said programmed entry data to a visual display on said housing to thereby identify the user, medicine and frequency of the programmed data, means in the form of clock signals responsive to the programmed frequency data and audible signal means responsive to the clock means for indicating when the programmed time frequency has elapsed thereby alerting the user that additional medication may be necessary.

13. An electronic system according to claim 12, wherein the data concerning the additional medication is recalled and visually displayed by the manual activation of a switch.

14. An electronic system according to claim 12, wherein a plurality of selected time frequencies and medications can be stored in the device for recall at a later time.

15. An electronic system according to claim 12, wherein all program entry data is converted into binary data and then converted into LED or LCD visual display.

16. An electronic system according to claim 12, wherein a group of persons can be monitored by the programmed entry of individual identification codes.

17. An electronic system according to claim 16, wherein a plurality of medications can be monitored by the programmed entry of medication codes.

18. An electronic system according to claim 12, wherein the device is battery powered and includes a stand-by or back-up battery system activated when the power of the main battery is insufficient to power the device.

19. An electronic system according to claim 12, wherein the visual display of the data is in numerical form.

20. An electronic system according to claim 12, wherein the visual display of the data is in alphanumeric form.

21. An electronic system according to claim 12, wherein visual display data is provided indicating the number of dosages already taken by the user, of a particular kind of medication.

22. An electronic system according to claim 12, wherein visual display data is provided indicating the number of days remaining for the user to take the prescribed medication.

* * * * *